United States Patent
Bellec et al.

(10) Patent No.: US 11,763,233 B2
(45) Date of Patent: Sep. 19, 2023

(54) METHOD, APPARATUS AND COMPUTER PROGRAM PRODUCT FOR PRIORITIZING A DATA PROCESSING QUEUE

(71) Applicant: Optum Services (Ireland) Limited, Dublin (IE)

(72) Inventors: Jacques Bellec, Dublin (IE); Elizabeth Mae Obee, New Orleans, LA (US); David T. Cleere, Kilkenny (IE)

(73) Assignee: Optum Services (Ireland) Limited, Dublin (IE)

( * ) Notice: Subject to any disclaimer, the term of this patent is extended or adjusted under 35 U.S.C. 154(b) by 585 days.

(21) Appl. No.: 16/774,729

(22) Filed: Jan. 28, 2020

(65) Prior Publication Data
US 2021/0089931 A1    Mar. 25, 2021

Related U.S. Application Data

(60) Provisional application No. 62/903,009, filed on Sep. 20, 2019.

(51) Int. Cl.
| | |
|---|---|
| *G06Q 10/0635* | (2023.01) |
| *G16H 40/20* | (2018.01) |
| *G06N 5/02* | (2023.01) |
| *G06F 16/332* | (2019.01) |
| *G06F 40/20* | (2020.01) |
| *G06Q 10/0631* | (2023.01) |
| *G06F 16/21* | (2019.01) |

(52) U.S. Cl.
CPC ......... *G06Q 10/0635* (2013.01); *G06F 16/21* (2019.01); *G06F 16/3329* (2019.01); *G06F 40/20* (2020.01); *G06N 5/02* (2013.01); *G06Q 10/0631* (2013.01); *G16H 40/20* (2018.01)

(58) Field of Classification Search
CPC .................................................. G06Q 10/0635
See application file for complete search history.

(56) References Cited

U.S. PATENT DOCUMENTS

| | | | |
|---|---|---|---|
| 10,366,378 B1 * | 7/2019 | Han | G06Q 20/204 |
| 11,288,240 B1 * | 3/2022 | Sayad | G06Q 30/0241 |
| 2011/0282695 A1 | 11/2011 | Blue | |

(Continued)

FOREIGN PATENT DOCUMENTS

WO      2003/071388 A2      8/2003

OTHER PUBLICATIONS

Aral et al, A prescription fraud detection model, Computer Methods and Programs in Biomedicine, vol. 106, Issue 1, Apr. 2012, pp. 37-46 (Year: 2012).*

(Continued)

*Primary Examiner* — Andre D Boyce
(74) *Attorney, Agent, or Firm* — Alston & Bird LLP

(57) ABSTRACT

Methods, apparatus, systems, computing devices, computing entities, and/or the like for programmatically prioritizing a data processing queue are provided. An example method may include retrieving a plurality of data objects in the data processing queue, generating a base data table based at least in part on the plurality of data objects, determining a predictive data model based at least in part on the base data table, and adjusting a queue order of the plurality of data objects in the data processing queue based at least in part on a risk score calculated by the predictive data model.

20 Claims, 12 Drawing Sheets

(56) References Cited

U.S. PATENT DOCUMENTS

| | | | |
|---|---|---|---|
| 2013/0006668 A1 | 1/2013 | Van Arkel et al. | |
| 2014/0149144 A1* | 5/2014 | Li | G06Q 10/10 |
| | | | 705/4 |
| 2016/0110512 A1 | 4/2016 | Adjaoute | |
| 2017/0006135 A1* | 1/2017 | Siebel | G06N 20/00 |
| 2017/0038919 A1* | 2/2017 | Moss | G06F 3/04817 |
| 2017/0124176 A1* | 5/2017 | Beznos | G06F 16/254 |
| 2017/0270435 A1 | 9/2017 | Gallardo | |
| 2018/0239870 A1 | 8/2018 | Goldman et al. | |
| 2020/0250571 A1* | 8/2020 | Almasan | G06Q 30/018 |

OTHER PUBLICATIONS

B. Nithya et al, Predictive Analytics in Health Care Using Machine Learning Tools and Techniques, International Conference on Intelligent Computing and Control Systems, pp. 492-499 (Year: 2017).*

"How To Report Fraud and Suspected Fraud," Centers for Medicare & Medicaid Services, CMS. gov, pp. 1-3, [article], [online]. [Retrieved from the Internet Apr. 8, 2020] <https://www.cms.gov/Medicare-Medicaid-Coordination/Fraud-Prevention/FraudAbuseforConsumers/Report_Fraud_and_Suspected_Fraud>.

Joudaki, Hossein et al. "Using Data Mining To Detect Health Care Fraud and Abuse: A Review Of Literature," Global Journal of Health Science, vol. 7, No. 1, (2015), pp. 194-202. ISSN: 1916-9736. E-ISSN: 1916-9744.

* cited by examiner

| STATUS | TIP ID | RISK CATEGORY | PROVIDER ID | PROVIDER NAME | COUNT TIPS | STATE | DAYS OPEN | RISK SCORE | INVESTIGATOR |
|---|---|---|---|---|---|---|---|---|---|
| IN PROGRESS | 125441 | HIGH | 885423 | ABC PHARMACY | 2 | NC | 1 | 983 | BELLA |
| IN PROGRESS | 545868 | HIGH | 444574 | ST. M HOSPITAL | 2 | CA | 1 | 970 | BELLA |
| IN PROGRESS | 452854 | HIGH | 555742 | JOHN DOE | 1 | NY | 6 | 960 | JOSE |
| IN PROGRESS | 744234 | HIGH | 868345 | RSM PHARMACY | 1 | CA | 8 | 960 | JOSE |
| IN PROGRESS | 452143 | MEDIUM | 867324 | SSS HOSPITAL | 1 | NY | 10 | 959 | SARA |
| IN PROGRESS | 444527 | MEDIUM | 336512 | JAN DOE | 1 | NC | 10 | 940 | RAY |
| NOT STARTED | 441345 | MEDIUM | 553412 | ADAM AKIN MD | 1 | MI | 22 | 954 | JOHN |
| NOT STARTED | 886571 | LOW | 669543 | HEALTH HOSPITAL | 1 | MI | 34 | 950 | JOSE |
| NOT STARTED | 336942 | LOW | 333216 | P'S PHARMACY | 1 | NY | 34 | 950 | SARA |
| NOT STARTED | 798521 | LOW | 112453 | DAVID CARIN | 1 | CA | 10 | 940 | JOHN |
| NOT STARTED | 223546 | LOW | 669845 | EVAN WILSON MD | 1 | MI | 8 | 935 | RAY |

| STATUS | TIP ID | RISK CATEGORY | PROVIDER ID | PROVIDER NAME | COUNT TIPS | STATE | DAYS OPEN | RISK SCORE | INVESTIGATOR |
|---|---|---|---|---|---|---|---|---|---|
| IN PROGRESS | 125441 | HIGH | 885423 | ABC PHARMACY | 2 | NC | 1 | 983 | BELLA |

| ALLEGATION | ALLEGATION DESCRIPTION |
|---|---|
| UNABLE TO VALIDATE DEMOGRAPHIC INFORMATION (E.G. LOCATION, PHONE NUMBER OR LICENSE INFORMATION) | RX PHARMACY INVESTIGATION, CASE #112543 |

QUEUE OVERVIEW
TIP QUEUE
TIP DETAIL

TIP DETAILS

INVESTIGATION TIMELINE

SUN 3  MON 4  TUE 5  WED 6  THU 7  FRI 8  SAT 9  SUN 10  MON 11

INFO RECEIVED DATE
SYSTEM ENTRY DATE
PROCESSING DATE

ASSOCIATED MEMBER TIPS
LINKED TIP INFO

1

METHOD, APPARATUS AND COMPUTER PROGRAM PRODUCT FOR PRIORITIZING A DATA PROCESSING QUEUE

CROSS-REFERENCE TO RELATED APPLICATION

The present application claims priority to and benefit of U.S. Provisional Patent Application No. 62/903,009, filed on Sep. 20, 2019, the entire content of which is incorporated by reference into the present application.

TECHNOLOGICAL FIELD

Embodiments of the present disclosure generally relate to a data processing queue. For example, various embodiments of the present disclosure may programmatically prioritizing data objects in the data processing queue for a healthcare fraud, waste, and abuse (FWA) investigation system.

BACKGROUND

Applicant has identified many technical challenges, deficiencies and problems associated with prioritizing a data processing queue, including when the data processing queue is implemented in a healthcare FWA investigation system for processing lead(s), tip(s), and/or allegation(s) related to suspected healthcare FWA.

Healthcare FWA may involve physicians, pharmacists, beneficiaries, and even medical equipment companies. Success in combating healthcare FWA is measured not only by convictions, but also by effective deterrent efforts. As such, anyone suspecting healthcare FWA (for example, Medicaid fraud, waste, or abuse) may be encouraged to report it.

Healthcare FWA investigators may receive a large amount of leads, tips, and/or allegations from whistleblowers and may be obliged to investigate them. In some examples, such leads may originate from multiple sources, and may contain more or less information to characterize the abnormal behavior. For example, lead sources may include insurance plan members who receive an explanation of benefits that do not match the services they received, whistleblower employees or associates of dishonest providers, media leads, and government agency leads (e.g., leads from the Office of Inspector General (OIG)). While most leads may not end up with any actions taken, the ever-growing number of leads means that some opportunities may be missed due to the lag between when the lead is received and when it is investigated. As such, there is a need for prioritizing the leads such that appreciate action can be taken in time.

BRIEF SUMMARY

In general, embodiments of the present disclosure provide methods, apparatus, systems, computing devices, computing entities, and/or the like.

In accordance with one aspect, an apparatus for prioritizing a data processing queue is provided. The apparatus may comprise at least one processor and at least one non-transitory memory comprising a computer program code. The at least one non-transitory memory and the computer program code may be configured to, with the at least one processor, cause the apparatus to: retrieve a plurality of data objects in the data processing queue; generate a base data table based at least in part on the plurality of data objects; determine a predictive data model based at least in part on the base data table; and adjust a queue order of the plurality of data objects in the data processing queue based at least in part on a risk score calculated by the predictive data model. In some examples, each of the plurality of data objects may comprise a text field. In some examples, the base data table may comprise one or more topic variables associated with the text field of each of the plurality of data objects.

In some examples, the plurality of data objects may be associated with a healthcare FWA investigation system. In some examples, the text field of each of the plurality of data objects may comprise a healthcare fraud lead description.

In some examples, when generating the base data table based at least in part on the plurality of data objects, the at least one non-transitory memory and the computer program code may be configured to, with the at least one processor, cause the apparatus to further: remove at least one of a punctuation element, a date element, or a Unicode element from the text field of each of the plurality of data objects.

In some examples, when generating the base data table based at least in part on the plurality of data objects, the at least one non-transitory memory and the computer program code may be configured to, with the at least one processor, cause the apparatus to further: remove at least one stop-word from the text field of each of the plurality of data objects.

In some examples, when generating the base data table based at least in part on the plurality of data objects, the at least one non-transitory memory and the computer program code may be configured to, with the at least one processor, cause the apparatus to further: calculate/determine/predict an optimal topic count number based on the text field of each of the plurality of data objects. In some examples, the one or more topic variables are associated with the optimal topic count number.

In some examples, when calculating the optimal topic count number, the at least one non-transitory memory and the computer program code may be configured to, with the at least one processor, cause the apparatus to further: determine a plurality of topic variables based at least in part on a natural language processing model and the text field of each of the plurality of data objects; and calculate/determine/predict a plurality of topic count number coherence scores associated with the plurality of topic variables, wherein the each of the plurality of topic count number coherence scores is associated with a topic count number.

In some examples, the natural language processing model may be a Latent Dirichlet Allocation (LDA) model.

In some examples, the at least one non-transitory memory and the computer program code may be configured to, with the at least one processor, cause the apparatus to further: determine a highest topic count number coherence score from the plurality of topic count number coherence scores; and select a corresponding topic count number associated with the highest topic count number coherence score as the optimal topic count number.

In some examples, when calculating the plurality of topic count number coherence scores associated with the plurality of topic variables, the at least one non-transitory memory and the computer program code may be configured to, with the at least one processor, cause the apparatus to further: select a first topic variable group from the plurality of topic variables, wherein the first topic variable group is associated with a first topic count number; calculate/determine/predict a topic coherence score for each topic variable in the first topic variable group; and calculate/determine/predict a first topic count number coherence score for the first topic count number based at least in part on the topic coherence score for each topic variable in the first topic variable group.

In some examples, the base data table may comprise at least one of: provider metric, lead metric, demographics, lead source, referral type, business area, allegation type, or taxonomy.

In some examples, when determining the predictive data model based at least in part on the base data table, the at least one non-transitory memory and the computer program code may be configured to, with the at least one processor, cause the apparatus to further: generate a plurality of predictive data models based at least in part on the base data table; calculate/determine/predict at least one performance metrics for each of the plurality of predictive data models; and select the predictive data model from the plurality of predictive data models based at least in part on the at least one performance metrics.

In some examples, the at least one non-transitory memory and the computer program code may be configured to, with the at least one processor, cause the apparatus to further: calculate/determine/predict a risk score for each of the plurality of data objects based at least in part on the predictive data model and a corresponding data object.

In accordance with one aspect, a computer-implemented method for programmatically prioritizing a data processing queue is provided. The computer-implemented method may comprise retrieving a plurality of data objects in the data processing queue, wherein each of the plurality of data objects comprises a text field; generating a base data table based at least in part on the plurality of data objects, wherein the base data table comprises one or more topic variables associated with the text field of each of the plurality of data objects; determining a predictive data model based at least in part on the base data table; and adjusting a queue order of the plurality of data objects in the data processing queue based at least in part on a risk score calculated by the predictive data model.

In accordance with one aspect, a computer program product may be provided. The computer program product may comprise at least one non-transitory computer-readable storage medium having computer-readable program code portions stored therein. The computer-readable program code portions may comprise an executable portion configured to: retrieve a plurality of data objects in the data processing queue, wherein each of the plurality of data objects comprises a text field; generate a base data table based at least in part on the plurality of data objects, wherein the base data table comprises one or more topic variables associated with the text field of each of the plurality of data objects; determine a predictive data model based at least in part on the base data table; and adjust a queue order of the plurality of data objects in the data processing queue based at least in part on a risk score calculated by the predictive data model.

The above summary is provided merely for purposes of summarizing some example embodiments to provide a basic understanding of some aspects of the disclosure. Accordingly, it will be appreciated that the above-described embodiments are merely examples. It will be appreciated that the scope of the disclosure encompasses many potential embodiments in addition to those here summarized, some of which will be further described below.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

Figure 8:
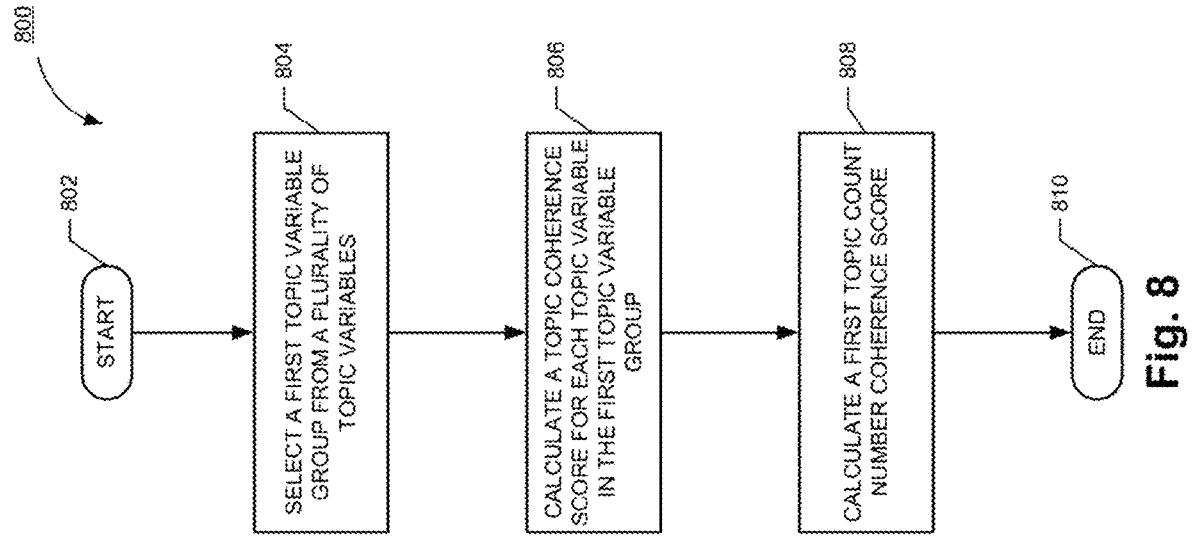
Figure 9:
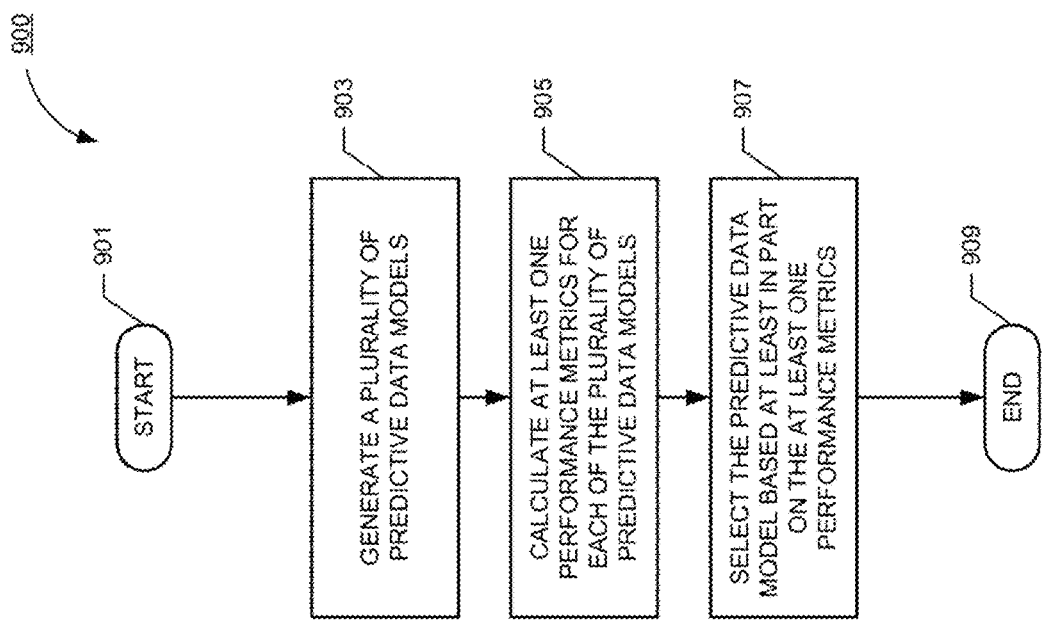
Figure 10:
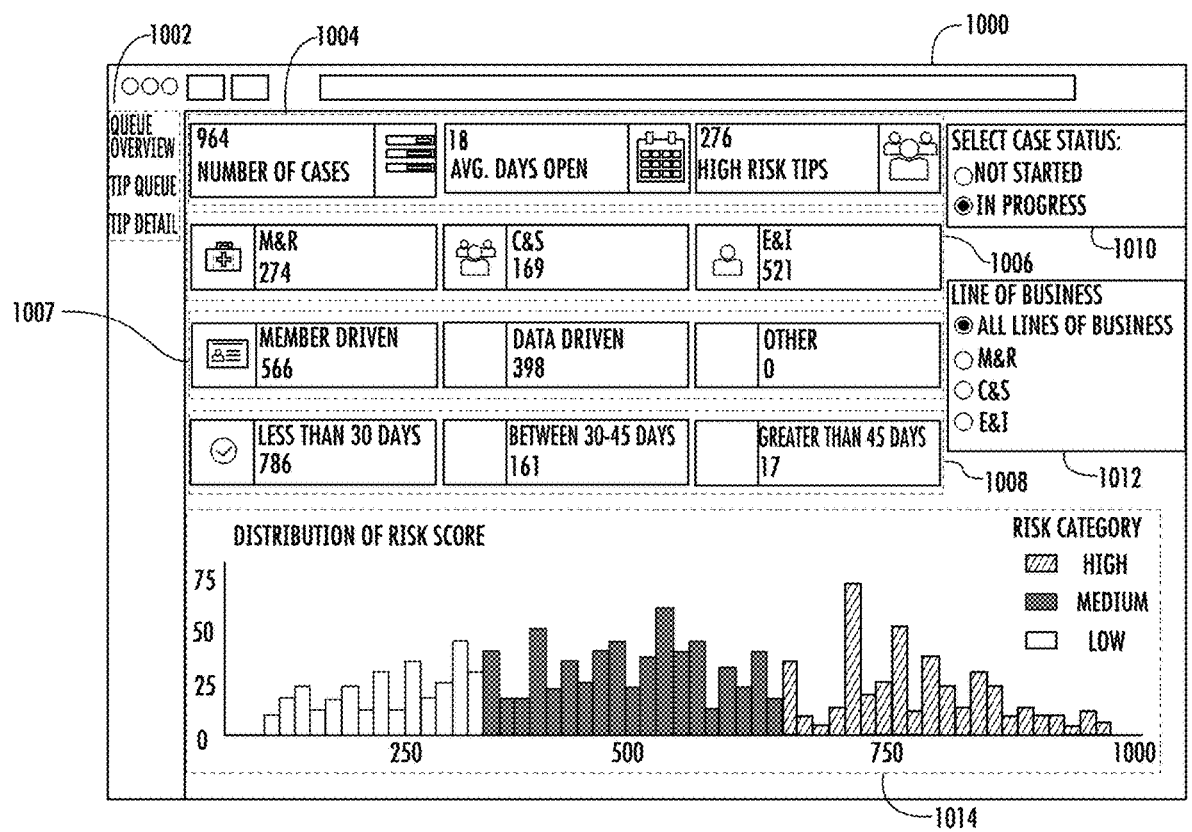

FIGS. 5, 6, 7, 8, and 9 provide example flowcharts illustrating example steps, processes, procedures, and/or operations associated with an example data processing system, in accordance with various embodiments of the present disclosure; and FIGS. 10, 11, and 12 provide example views of example user interfaces, in accordance with various embodiments of the present disclosure.

DETAILED DESCRIPTION OF SOME EXAMPLE EMBODIMENTS

Various embodiments of the present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

The phrases "in one embodiment," "according to one embodiment," and/or the like generally mean that the particular feature, structure, or characteristic following the phrase may be included in at least one embodiment of the present disclosure and may be included in more than one embodiment of the present disclosure (importantly, such phrases do not necessarily refer to the same embodiment).

I. COMPUTER PROGRAM PRODUCTS, METHODS, AND COMPUTING ENTITIES

Embodiments of the present disclosure may be implemented as computer program products that comprise articles of manufacture. Such computer program products may include one or more software components including, for example, applications, software objects, methods, data structures, and/or the like. A software component may be coded in any of a variety of programming languages. An illustrative programming language may be a lower-level programming language such as an assembly language associated with a particular hardware architecture and/or operating system platform/system. A software component comprising assembly language instructions may require conversion into executable machine code by an assembler prior to execution by the hardware architecture and/or platform/system. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Additionally, or alternatively, embodiments of the present disclosure may be implemented as a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media may include all computer-readable media (including volatile and non-volatile media).

In one embodiment, a non-volatile computer-readable storage medium may include a floppy disk, flexible disk, hard disk, solid-state storage (SSS) (e.g., a solid-state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

Figure 1:
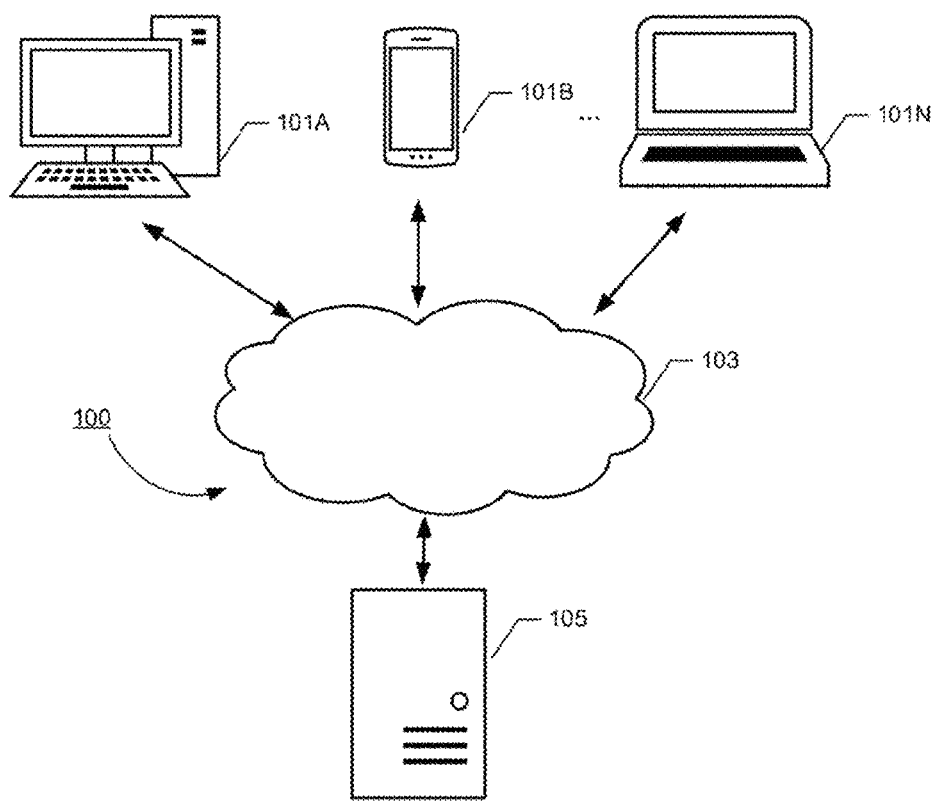
FIG. 1 is a diagram of an example data processing platform/system that can be used in accordance with various embodiments of the present disclosure.

FIG. 1 Provides an Illustration of a Data Processing Platform/System 100 that can be Used in conjunction with various embodiments of the present disclosure. As shown in FIG. 1, the data processing platform/system 100 may comprise one or more data object computing entities 105, one or more user computing entities 101A, 101B, . . . 101N, and one or more networks 103. Each of the components of the data processing platform/system 100 may be in electronic communication with, for example, one another over the same or different wireless or wired networks 103 including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

a. Exemplary Data Object Computing Entity

Figure 2:
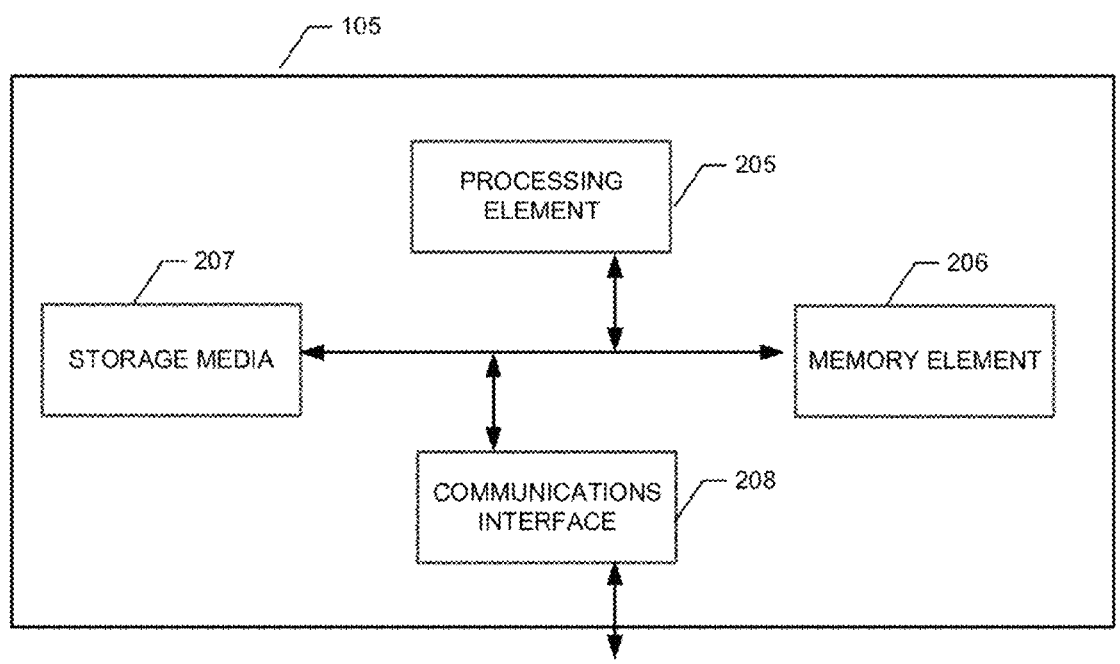
FIG. 2 is a schematic representation of an example data object computing entity in accordance with various embodiments of the present disclosure.

FIG. 2 provides a schematic of a data object computing entity 105 according to one embodiment of the present disclosure. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein. In one embodiment, these functions, operations, and/or processes can be performed on data, content, information, and/or similar terms used herein.

As indicated, in one embodiment, the data object computing entity 105 may also include one or more network and/or communications interfaces 208 for communicating with various computing entities, such as by communicating data, content, information, and/or similar terms used herein that can be transmitted, received, operated on, processed, displayed, stored, and/or the like. For instance, the data object computing entity 105 may communicate with other data object computing entities 105, one or more user computing entities 101A-101N, and/or the like.

As shown in FIG. 2, in one embodiment, the data object computing entity 105 may include or be in communication with one or more processing elements 205 (also referred to as processors, processing circuitry, and/or similar terms used herein interchangeably) that communicate with other elements within the data object computing entity 105 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the data object computing entity 105 may further include or be in communication with volatile media (also referred to as volatile storage, memory, memory storage, memory circuitry and/or similar terms used herein interchangeably). In one embodiment, the volatile storage or memory may also include one or more memory element 206 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory element 206 may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205 as shown in FIG. 2 and/or the processing element 308 as described in connection with FIG. 3. Thus, the databases, database instances, database management system entities, data, applications, programs, program modules, scripts, source code, object code, byte code, compiled code, interpreted code, machine code, executable instructions, and/or the like may be used to control certain aspects of the operation of the data object computing entity 105 with the assistance of the processing element 205 and operating system.

In one embodiment, the data object computing entity 105 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or storage media 207 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or storage media 207 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Storage media 207 may also be embodied as a data storage device or devices, as a separate database server or servers, or as a combination of data storage devices and separate database servers. Further, in some embodiments, storage media 207 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery prediction system may be stored. Further, the information/data required for the operation of the recovery prediction system may also be partially stored in the cloud data storage system and partially stored in a locally maintained data storage system. More specifically, storage media 207 may encompass one or more data stores configured to store information/data usable in certain embodiments.

As indicated, in one embodiment, the data object computing entity 105 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the data object computing entity 105 may communicate with computing entities or communication interfaces of other data object computing entities 105, user computing entities 101A-101N, and/or the like.

As indicated, in one embodiment, the data object computing entity 105 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data object computing entity 105 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The data object computing entity 105 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the data object computing entity's components may be located remotely from other data object computing entity 105 components, such as in a distributed system. Furthermore, one or more of the components may be aggregated and additional components performing functions described herein may be included in the data object computing entity 105. Thus, the data object computing entity 105 can be adapted to accommodate a variety of needs and circumstances.

b. Exemplary User Computing Entity

Figure 3:
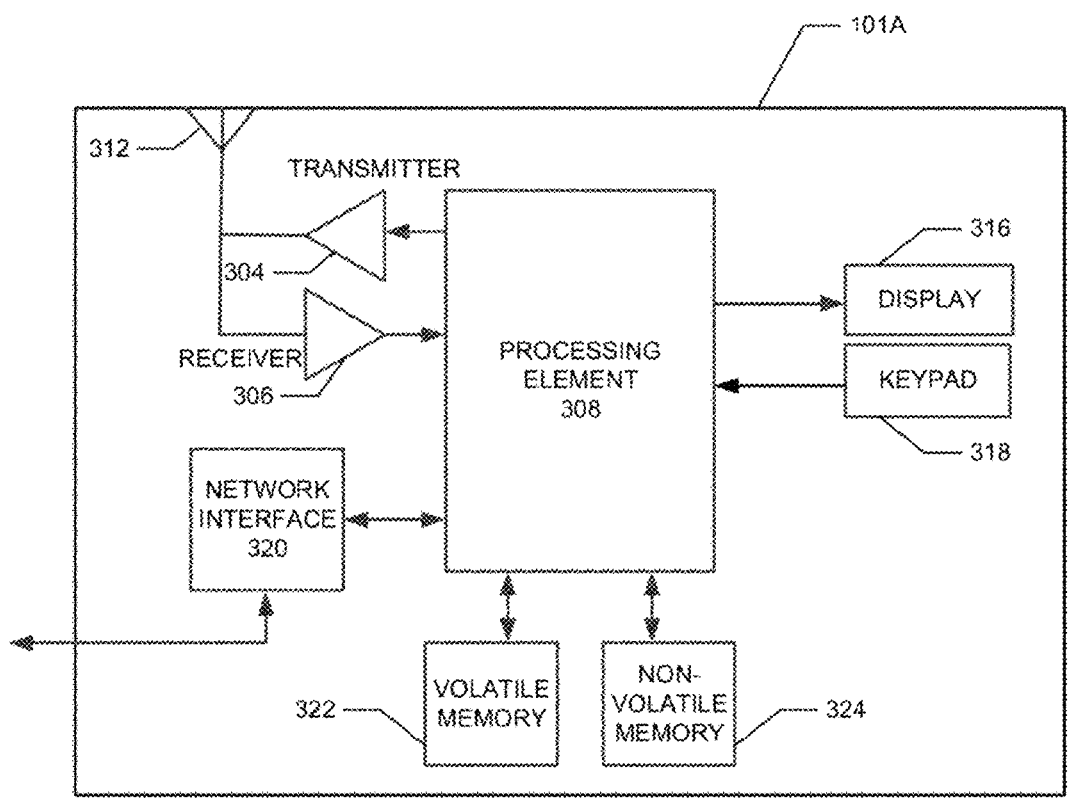
FIG. 3 is a schematic representation of an example user computing entity in accordance with various embodiments of the present disclosure.

FIG. 3 provides an illustrative schematic representative of one of the user computing entities 101A to 101N that can be used in conjunction with embodiments of the present disclosure. As will be recognized, the user computing entity may be operated by an agent and include components and features similar to those described in conjunction with the data object computing entity 105. Further, as shown in FIG. 3, the user computing entity may include additional components and features. For example, the user computing entity 101A can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a data object computing entity 105, another user computing entity 101A, and/or the like. In this regard, the user computing entity 101A may be capable of operating with one or more air interface standards, communication protocols, modulation types, and access types. More particularly, the user computing entity 101A may comprise a network interface 320, and may operate in accordance with any of a number of wireless communication standards and protocols. In a particular embodiment, the user computing entity 101A may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 101A can communicate with various other entities using Unstructured Supplementary Service data (USSD), Short Message Service (SMS), Multimedia Messaging Service (MIMS), Dual-Tone Multi-Frequency Signaling (DTMF), Subscriber Identity Module Dialer (SIM dialer), and/or the like. The user computing entity 101A can also download changes, add-ons, and updates, for instance, to its firmware, software (e.g., including executable instructions, applications, program modules), and operating system.

According to one embodiment, the user computing entity 101A may include location determining aspects, devices, modules, functionalities, and/or similar words used herein interchangeably. For example, the user computing entity 101A may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 101A may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 101A may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 101A to cause display or audible presentation of information/data and for user interaction therewith via one or more user input interfaces. The user output interface may be updated dynamically from communication with the data object computing entity 105. The user input interface can comprise any of a number of devices allowing the user computing entity 101A to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 101A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 101A can collect information/data, user interaction/input, and/or the like.

The user computing entity 101A can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entities 101A-101N.

c. Exemplary Networks

In one embodiment, the networks 103 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 103 may have any suitable communication range associated therewith and may include, for example, global networks (e.g., the Internet), MANs, WANs, LANs, or PANs. In addition, the networks 103 may include medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms/systems provided by network providers or other entities.

Further, the networks 103 may utilize a variety of networking protocols including, but not limited to, TCP/IP based networking protocols. In some embodiments, the protocol is a custom protocol of JSON objects sent via a Websocket channel. In some embodiments, the protocol is JSON over RPC, JSON over REST/HTTP, and/or the like.

III. EXEMPLARY OPERATION

Reference will now be made to FIGS. 5, 6, 7, 8, 9, 10, 11, and 12. FIGS. 5, 6, 7, 8, and 9 provide flowcharts illustrating example steps, processes, procedures, and/or operations associated with a data processing platform/system in accordance with various embodiments of the present disclosure. FIGS. 10, 11, and 12 provide example views of interactive user interfaces in accordance with various embodiments of the present disclosure.

While example embodiments of the present disclosure may be described in the healthcare FWA investigation context, as will be recognized, embodiments of the present invention are not limited to this context only.

a. Exemplary Data Processing Queue Prioritization

As described above, healthcare FWA investigators may receive a large amount of leads, tips, and/or allegations associated with suspected healthcare FWA. In some examples, the lead may indicate a potential issue across the entire activity of a provider, specific to particular types of services, or relevant to only a single member who has seen the provider. As such, it can be technical challenging to manage leads so that the strongest leads may be reviewed and/or investigated first.

To address these technical challenges, example embodiments of the present disclosure may generate a data object and may generate a data processing queue for processing a plurality of data objects.

In the present disclosure, the term "data object" refers to a data structure that represents one or more functionalities and/or characteristics associated with data and/or information. For example, a data object associated with a healthcare FWA investigation system may represent a lead, a tip, and/or an allegation associated with suspected healthcare FWA. In some examples, a data object may be generated by a computing entity (such as the data object computing entity 105 described above in connection with FIG. 1 and FIG. 2). In some examples, a data object may be generated based on one or more inputs received from a user (such as through a user computing entity described above).

In the present disclosure, the term "data processing queue" refers to a collection of data objects that may be arranged in a queue order for processing. For example, a computing entity (such as the data object computing entity 105 described above in connection with FIG. 1 and FIG. 2) may retrieve data objects from the data processing queue for processing based on their queue orders. In some examples, a data object having a higher queue order may be processed before a data object having a lower queue order. In some examples, the computing entity may cause the rendering of the data object for display on a user computing entity, and may receive one or more user inputs associated with the data object via the user computing entity, details of which are described herein.

Figure 4:
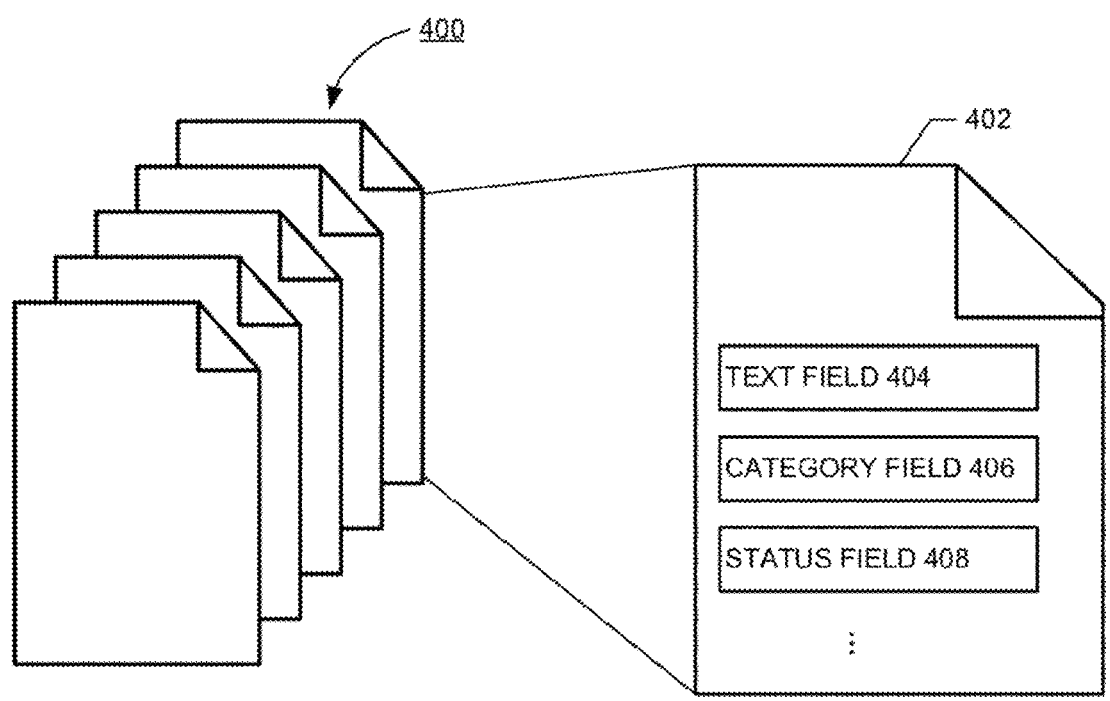
FIG. 4 is a schematic representation of an example data processing queue and an example data object in accordance with various embodiments of the present disclosure.

Referring now to FIG. 4, an example diagram illustrates an example data processing queue 400 and an example data object 402.

In the example shown in FIG. 4, the example data object 402 may comprise a text field 404. In some examples, the text field may comprise a text string, an American Standard Code for Information Interchange (ASCII) text, a pointer, a memory address, and/or the like.

In some examples, the text field 404 may comprise an allegation description received from a user computing device. In some examples, the allegation description may provide a description of a lead, a tip, and/or an allegation associated with a healthcare FWA. For example, the allegation description may describe whether a suspected provider participates in an insurance network or has submitted out of network claims. Additionally, or alternatively, the allegation description may describe data analytics of data patterns that may be, for example, submitted by an employee who observes unusual claims during the course of his job duties or through specific investigation for fraud, waste, abuse and error (FWAE) providers, or generated through a machine learning model that may be configured to conduct pattern recognition analysis (for example, through supervised or unsupervised learning).

In some examples, the text field 404 may be generated based on a user input received from a member of an insurance network or a healthcare provider via a computing entity (such as a user computing entity described above). Additionally, or alternatively, the text field 404 may be generated through other means, including but not limited to, a data object computing entity as described above.

In some examples, when generating the example data processing queue 400 based on one or more data objects (such as the data object 402 shown in FIG. 4), a computing entity (such as the data object computing entity 105 described above in connection with FIG. 1 and FIG. 2) may conduct preliminary analysis on the one or more data objects. For example, the computing entity may determine whether there is any duplicate in the one or more data objects. The computing entity may determine that a data object is a duplicate of another data object when they comprise the same or similar text fields. In this example, the computing entity may remove the duplicate data object from the data processing queue 400. In other words, the computing entity may identify any duplicate leads, tips, and/or allegations that have been submitted to, for example, the data processing platform/system as described above, and therefore may reduce the computing resource usage associated with data processing.

Additionally, or alternatively, the computing entity may conduct preliminary analysis on the one or more data objects based on one or more manual review of the data objects. For example, a user (such as a Healthcare FWA investigator) may label one or more data objects as "closed without finding," which may indicate that a manual review of the data object (for example, the text field of the data object describing a lead, a tip, and/or an allegation) may determine that no action needs to be taken with regards to the lead, tip, and/or allegation. As an example, the user may determine that the lead, the tip, and/or the allegation has previously been processed and/or is a duplicate of another lead/tip/allegation. In this example, the computing entity may remove the data object labeled with "closed without finding" from the data processing queue.

In the example shown in FIG. 4, the example data object 402 may comprise a category field 406. In some examples, the category field 406 may indicate a line of business associated with the lead(s), tip(s), and/or allegation(s). Example line of business may include, but not limited to, Medicare and retirement (M&R), community and state (C&S), employer and individual (E&I). Additionally, or alternatively, the category field 406 may indicate a category of the lead, tip or allegation associated with the example data object 402. For example, the category field 406 may indicate the source of the lead, tip, or allegation (for example, from a member of an insurance network, from a healthcare provider, through data analytics as described above). In some examples, the category field 406 may comprise a text string, an ASCII text, a pointer, a memory address, and/or the like.

In the example shown in FIG. 4, the example data object may comprise a status field 408. The status field 408 may comprise a text string, an ASCII text, a pointer, a memory address, and/or the like, which may, for example, indicate that the data object is being/has been processed ("in progress") or that the data object has not been processed ("not started").

In some examples, the example data object 402 may comprise one or more additional fields. For example, the example data object 402 may comprise an identifier field. The identifier field may comprise a text string, an ASCII text, a pointer, a memory address, and/or the like, which may uniquely identify a data object from the plurality of data objects in the data processing queue.

In some examples, the example data object may comprise a provider name field. The provider name field may comprise a text string, an ASCII text, a pointer, a memory address, and/or the like, which may indicate a name of the healthcare provider that may be suspected of healthcare FWA in the lead(s), tip(s), and/or allegation(s).

In some examples, the example data object may comprise a provider identifier field. The provider identifier field may comprise a text string, an ASCII text, a pointer, a memory address, and/or the like, which may uniquely identify the healthcare provider that may be suspected of healthcare FWA in the lead(s), tip(s), and/or allegation(s).

In some examples, the example data object may comprise a lead source field. The lead source field may comprise a text string, an ASCII text, a pointer, a memory address, and/or the like, which may indicate a source of the lead(s), tip(s), and/or allegation(s) that the data object may represent. Example sources may include, but not limited to, from a member, from the OIG, etc.

In some examples, the example data object may comprise a referral type field. The referral type field may comprise a text string, an ASCII text, a pointer, a memory address, and/or the like, which may indicate a referral type of the lead(s), tip(s), and/or allegation(s). For example, the referral type may be data analytics (such as claims data pattern described above). As another example, the referral type may indicate that the lead(s), tip(s), and/or allegation(s) may be referred to by a facility.

In some examples, the example data object may comprise an investigator field. The investigator field may comprise a text string, an ASCII text, a pointer, a memory address, and/or the like, which may indicate a name of an investigator who has been assigned to investigate the lead(s), tip(s), and/or allegation(s).

In some examples, additional fields of the example data object may be generated and/or updated. For example, example predictive modeling in accordance with embodiments of the present disclosure may determine a risk score and/or a risk category associated with the example data object. In some examples, subsequent to the example predictive modeling process, the example data object may be updated to include a risk category field. The risk category field may comprise a text string, an ASCII text, a pointer, a memory address, and/or the like, which may indicate a risk category ("high," "medium," "low") associated with the lead(s), tip(s), and/or allegation(s) based on the results of the example predictive modeling process, details of which are described herein. In some examples, subsequent to the example predictive modeling process, the example data object may be updated to include a risk score field. The risk score field may comprise a number, a text string, an ASCII text, a pointer, a memory address, and/or the like, which may indicate a risk score associated with the data object based on the results of the example predictive modeling process, details of which are described herein.

While FIG. 4 and the above description illustrate some example fields associated with an example data object, it is noted that the scope of the present disclosure is not limited to these data fields. In some examples, a data object may comprise data field(s) that are less than or more than those data fields described above.

Figure 5:
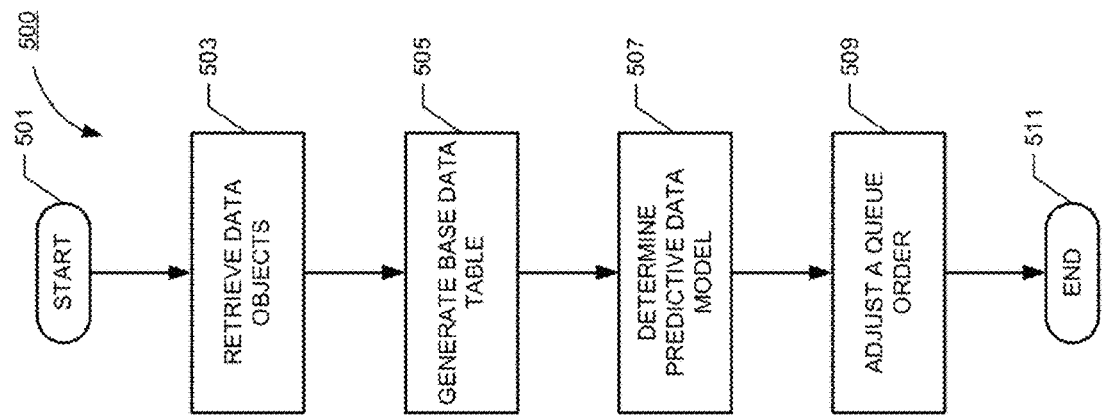

Referring now to FIG. 5, an example method 500 illustrates example prioritization of example data processing queue in accordance with embodiments of the present disclosure.

The example method 500 may start at step/operation 501.

At step/operation 503, a computing entity (such as the data object computing entity 105 described above in connection with FIG. 1 and FIG. 2) may include means (such as the processing element 205 of the data object computing entity 105 described above in connection with FIG. 2) for retrieving a plurality of data objects in the data processing queue.

In some examples, the plurality of data objects may be stored in a storage device associated with the computing entity. For example, referring back to FIG. 2, the plurality of data objects may be stored in the storage media 207 of the data object computing entity 105. In some examples, the plurality of data objects may be stored in a storage device that is external to the data object computing entity. For example, the plurality of data objects may be stored in a data repository (such as a database) that is external to the data object computing entity 105 and/or the data processing platform/system as illustrated in FIG. 1. In such an example, the data repository may be in electronic communication with the data object computing entity 105, and the data object computing entity 105 may electronically retrieve the plurality of data objects from the data repository based on, for example, a user request received from a computing entity (such as the user computing entity described above).

As described above, each of the plurality of data objects may comprise a text field, which may comprise a healthcare fraud lead description. In such an example, the plurality of data objects may be associated with a healthcare FWA investigation system. For example, the data processing platform/system 100 may be a healthcare FWA investigation system that may be configured to analyze leads, tips, and/or allegations associated with suspected healthcare FWA.

At step/operation 505, a computing entity (such as the data object computing entity 105 described above in connection with FIG. 1 and FIG. 2) may include means (such as the processing element 205 of the data object computing entity 105 described above in connection with FIG. 2) for generating a base data table based at least in part on the plurality of data objects.

In the present disclosure, the term "base data table" refers to a data structure that may provide data and/or information for generating, training and/or selecting one or more machine learning models. In some examples, a base data table may arrange data and/or information in a tabular form (e.g., rows and columns). In some examples, a base data table may comprise one or more metrics for generating one or more machine learning models (such as a predictive data model). For example, the base data table may comprise one or more topic variables associated with the text field of each of the plurality of data objects. Example details of an example base data table (for example, determining the one or more topic variables) are described further herein, including in connection with at least FIG. 6, FIG. 7, and FIG. 8.

At step/operation 507, a computing entity (such as the data object computing entity 105 described above in connection with FIG. 1 and FIG. 2) may include means (such as the processing element 205 of the data object computing entity 105 described above in connection with FIG. 2) for determining a predictive data model based at least in part on the base data table.

In the present disclosure, the term "predictive data model" or "predictive modeling" refers to a computer software algorithm (and, in some example, computer hardware for executing the computer software algorithm) that may generate one or more prediction data based on one or more input data. In some examples, the prediction data may indicate an outcome, a trend, or a likelihood based on the input data.

For example, a predictive data model in accordance with examples of the present disclosure may be generated by a computing entity (such as the data object computing entity 105 described above in connection with FIG. 1 and FIG. 2) in a data processing platform/system (such as the data processing platform/system 100 described above in connection with FIG. 1). In some examples, a predictive data model may generate one or more "risk scores" for one or more data objects in the data processing platform/system. In some examples, when the data object represents a lead, a tip, and/or an allegation associated with suspected healthcare FWA, the risk score may indicate a likelihood of successful outcome associated with the lead, the tip, and/or the allegation. For example, a high risk score may indicate a high likelihood that the corresponding lead(s), tip(s), and/or allegation(s) may lead to an identification of an actual healthcare FWA. Example details of risk scores are described further herein, including in connection with at least FIG. 9.

In some examples, one or more types of predictive data models may be implemented in accordance with various examples of the present disclosure. For example, a predictive data model may comprise one or more machine learning models and/or artificial intelligence algorithms, such as, but not limited to, logistic regression model, gradient boosting machine (e.g., XGBoost, LightGBM, CatBoost), random forest, and/or naive Bayes. Additionally, or alternatively, a predictive data model may comprise linear regression, decision tree, support vector machine (SVM), k-nearest neighbors algorithm (k-NN), K-means clustering, and/or the like. In some examples, a computing entity (such as the data object computing entity 105 described above in connection with FIG. 1 and FIG. 2) may generate a plurality of predictive data models, and may select one predictive data model from the plurality of predictive data models through a "champion-challenger approach," example details of which are described in connection with at least FIG. 9.

Referring back to FIG. 5, at step/operation 509, a computing entity (such as the data object computing entity 105 described above in connection with FIG. 1 and FIG. 2) may include means (such as the processing element 205 of the data object computing entity 105 described above in connection with FIG. 2) for adjusting a queue order of the plurality of data objects in the data processing queue.

In some examples, the computing entity may adjust the queue order based at least in part on the predictive data model. For example, the predictive data model may generate a risk score for each data object. In some examples, if the data object represents a lead, a tip, and/or an allegation associated with suspected healthcare FWA, the risk score may indicate a likelihood of successful outcome of the corresponding lead, tip, and/or allegation (for example, a likelihood that actual healthcare FWA may be identified based on the lead, tip, and/or allegation). In these examples, a data object with a higher corresponding risk score may be assigned a higher queue order, such that the data object may be processed by a computing entity before a data object with a lower corresponding risk score (which may be assigned a lower queue order). Example details of predictive data models and risk scores are described herein, including in connection with at least FIG. 9.

Referring back to FIG. 5, the example method 500 may end at step/operation 511.

The example method 500 may provide various technical advantages in date processing. For example, when a risk score calculated/determined/predicted by a predictive data model is used to prioritize the data processing queue of data objects representing lead(s), tip(s), and/or allegation(s) associated with suspected healthcare FWA, faster and/or more timely actions may be taken on the leads with highest likelihood of a successful outcome, which may lead to more efficient usage of computing resources. Additionally, or alternatively, the example method 500 may provide more accurate results from processing data objects based on, for example, the risk scores associated with the data objects from the data processing queue.

b. Exemplary Base Data Table Generation

As described above, in some examples, a computing entity (such as the data object computing entity 105 described above in connection with FIG. 1 and FIG. 2) may generate one or more base data tables. In some examples, the base data table may comprise one or more topic variables associated with the plurality of data objects. In some examples, the one or more topic variables of the base data table may be associated with an optimal topic count number. In some examples, the computing entity may calculate/determine/predict the optimal topic count number through topic modeling based on the plurality of data objects in the data processing queue (for example, based on the text fields of the plurality of data objects).

Figure 6:
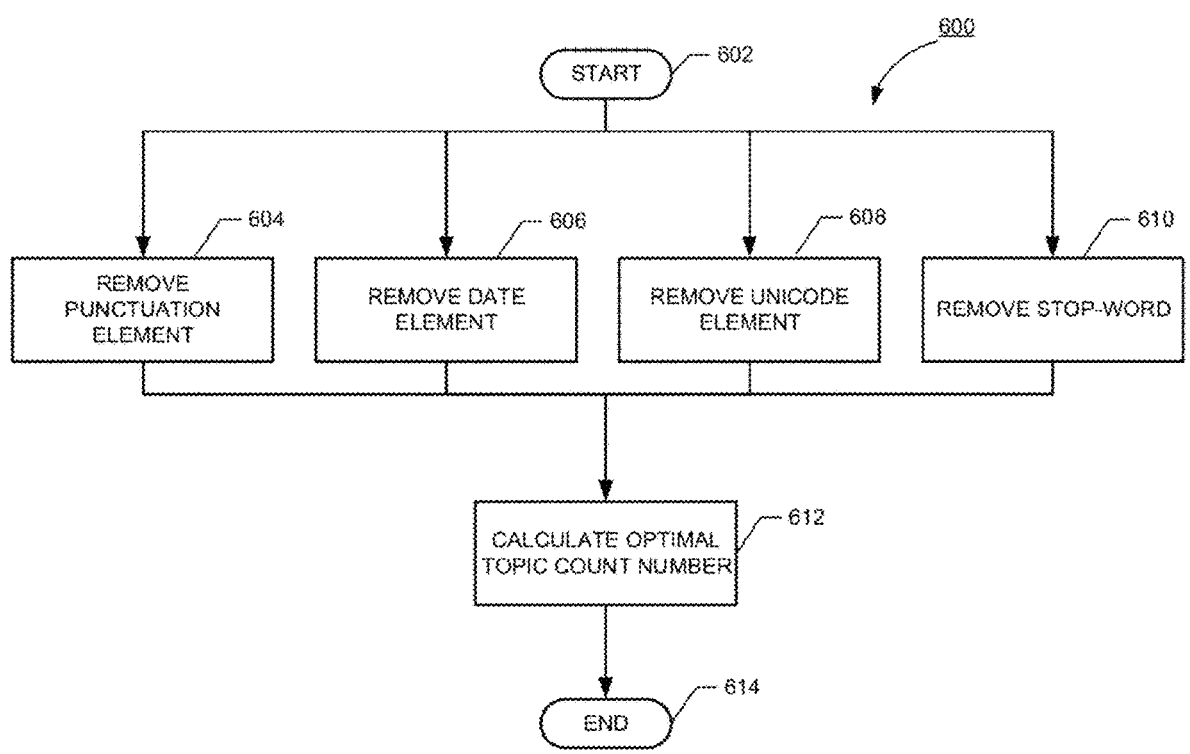

Referring now to FIG. 6, an example method 600 illustrates example operations of generating an example base data table in accordance with embodiments of the present disclosure.

The example method 600 may start at step/operation 602. In some examples, the step/operation 602 may be subsequent to step/operation 503 described above in connection with FIG. 5. In such examples, a computing entity (such as the data object computing entity 105 described above in connection with FIG. 1 and FIG. 2) may retrieve a plurality of data objects from a data processing queue, as described above.

At step/operation 604, a computing entity (such as the data object computing entity 105 described above in connection with FIG. 1 and FIG. 2) may include means (such as the processing element 205 of the data object computing entity 105 described above in connection with FIG. 2) for removing at least one punctuation element from the text field of each of the plurality of data objects.

As described above, a text field of a data object in accordance with examples of the present disclosure may comprise an allegation description. For example, the allegation description may provide a description of a lead, a tip, and/or an allegation associated with a healthcare FWA. In some examples, the allegation description may comprise one or more punctuation elements (for example, period, comma, parentheses). In such example, the computing entity may remove the punctuation elements from the text field at step/operation 604.

At step/operation 606, a computing entity (such as the data object computing entity 105 described above in connection with FIG. 1 and FIG. 2) may include means (such as the processing element 205 of the data object computing entity 105 described above in connection with FIG. 2) for removing at least one date element from the text field of each of the plurality of data objects. For example, a text field of a data object may comprise an allegation description that may provide a description of a lead, a tip, and/or an allegation associated with a healthcare FWA. In some examples, the allegation description may comprise one or more date elements (for example, a timestamp). In such example, the computing entity may remove the date elements from the text field at step/operation 606.

At step/operation 608, a computing entity (such as the data object computing entity 105 described above in connection with FIG. 1 and FIG. 2) may include means (such as the processing element 205 of the data object computing entity 105 described above in connection with FIG. 2) for removing at least one Unicode element from the text field of each of the plurality of data objects. For example, a text field of a data object may comprise an allegation description that may provide a description of a lead, a tip, and/or an allegation associated with a healthcare FWA. In some examples, the allegation description may comprise one or more Unicode elements (for example, a character that is not part of an English alphabet). In such example, the computing entity may remove the Unicode elements from the text field at step/operation 608.

At step/operation 610, a computing entity (such as the data object computing entity 105 described above in connection with FIG. 1 and FIG. 2) may include means (such as the processing element 205 of the data object computing entity 105 described above in connection with FIG. 2) for removing at least one stop-word from the text field of each of the plurality of data objects. In some examples, a stop-word may be a state-of-being verb (e.g., am, is, are). In some examples, a stop-word may be a common word in a domain associated with the data processing platform/system. For example, when the data processing platform/system is implemented in a healthcare FWA investigation system, stop-word may include, but not limited to, "claim," "member", and "provider." In some examples, the computing entity may programmatically determine one or more stop-words based on the topic variables associated with text fields of the plurality of data objects. Example details of topic variables are described further herein.

While step/operation 604, step/operation 606, step/operation 608, and step/operation 610 describe example steps and/or operations for preparing and/or cleansing data objects for generating an example base data table, it is noted that scope of the present disclosure is not limited to these steps. In some examples, additional and/or alternative step/operation(s) may be implemented.

For example, a computing entity (such as the data object computing entity 105 described above in connection with FIG. 1 and FIG. 2) may include means (such as the processing element 205 of the data object computing entity 105 described above in connection with FIG. 2) for removing whitespace from the text field of each of the plurality of data objects.

Additionally, or alternatively, a computing entity (such as the data object computing entity 105 described above in connection with FIG. 1 and FIG. 2) may include means (such as the processing element 205 of the data object computing entity 105 described above in connection with FIG. 2) for removing Uniform Resource Locator (URL) from the text field of each of the plurality of data objects.

Additionally, or alternatively, a computing entity (such as the data object computing entity 105 described above in connection with FIG. 1 and FIG. 2) may include means (such as the processing element 205 of the data object computing entity 105 described above in connection with FIG. 2) for changing texts from the text field of each of the plurality of data objects to lowercase.

At step/operation 612, a computing entity (such as the data object computing entity 105 described above in connection with FIG. 1 and FIG. 2) may include means (such as the processing element 205 of the data object computing entity 105 described above in connection with FIG. 2) for calculating an optimal topic count number.

In the present disclosure, the term "topic" or "topic variable" refers to a pattern or cluster of word(s) that may occur frequently in one or more text field(s). The term "topic count number" refers to a numeric amount of topic variable(s) that may be generated or chosen for the one or more text field(s). The term "optimal topic count number" refers to an optimal amount of topic variables that may best represent the meaning and/or context of the one or more text field(s).

In some examples, the computing entity may calculate/determine/predict the optimal topic count number based on the text field of each of the plurality of data objects after step/operation 604, step/operation 606, step/operation 608, and/or step/operation 610. For example, the optimal topic count number may be calculated/determined/predicted based on text fields where punctuation element(s), date element(s), Unicode element(s) and/or stop-word element(s) have been removed.

Figure 7:
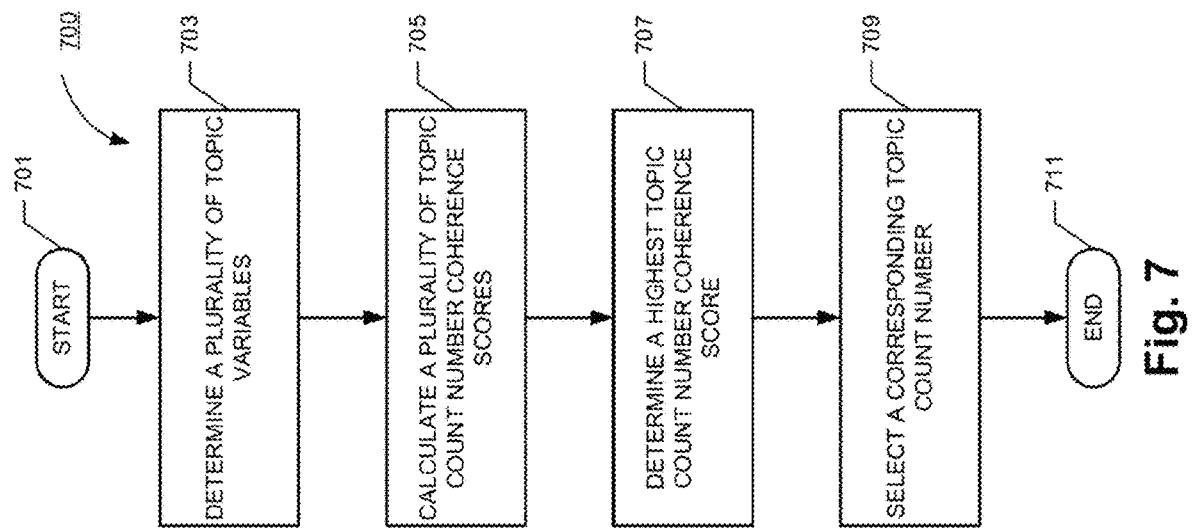

Referring now to FIG. 7, an example method 700 illustrates example operations of calculating an optimal topic count number in accordance with embodiments of the present disclosure.

The example method 700 may start at step/operation 701. In some examples, the step/operation 701 may be subsequent to step/operation 604, step/operation 606, step/operation 608, and/or step/operation 610 of FIG. 6, where punctuation element(s), date element(s), Unicode element(s) and/or stop-word element(s) have been removed from the text fields of the plurality of data objects.

At step/operation 703, a computing entity (such as the data object computing entity 105 described above in connection with FIG. 1 and FIG. 2) may include means (such as the processing element 205 of the data object computing entity 105 described above in connection with FIG. 2) for determining a plurality of topic variables associated with a plurality of data objects.

In some examples, the computing entity may determine the plurality of topic variables based at least in part on a natural language processing model and the text field of each of the plurality of data objects.

For example, the computing entity may implement a Latent Dirichlet Allocation (LDA) model as the natural language processing model. The LDA model may receive the text field of each of the plurality of data objects as input. The LDA model may analyze the co-occurrences of words in the text field. For example, the LDA model may implement a "bag-of-word" framework, which may calculate/determine/predict the frequency of each word in the text field regardless of the order that these words may appear in. In some examples, the LDA model may assign a probability of each word as a topic variable.

In some examples, the computing entity may generate the LDA model based on Gensim, which is an open-source software library for unsupervised topic modeling and natural language processing in Python. Additionally, or alternatively, the computing entity may generate the LDA model based on other software libraries.

While the above description illustrates an LDA model as an example natural language processing model, it is noted that the scope of the present disclosure is not limited to LDA model only. In some examples, other machine learning model(s), statistical model(s), and/or natural language processing model(s) may be used in addition to or in alternative of the LDA model, including, but is not limited to, hierarchical latent tree analysis (HLTA) model.

Referring back to FIG. 7, at step/operation 705, a computing entity (such as the data object computing entity 105 described above in connection with FIG. 1 and FIG. 2) may include means (such as the processing element 205 of the data object computing entity 105 described above in connection with FIG. 2) for calculating a plurality of topic count number coherence scores associated with the plurality of topic variables.

In the present disclosure, the term "topic count number coherence score" refers to a value that may represent a coherence level associated with a certain number of topic variables for one or more text fields. In other words, each topic count number coherence score may be associated with a topic count number (i.e. a certain amount of topic variables). For example, a computing entity (such as the data object computing entity 105 described above in connection with FIG. 1 and FIG. 2) may calculate/determine/predict a topic count number coherence score for a topic count number of fourteen. In this example, the computing entity may choose fourteen topic variables from, for example, the plurality of topic variables determined at step/operation 703, and may calculate/determine/predict a topic count number coherence score based on these fourteen topic variables.

Referring now to FIG. 8, an example method 800 illustrates example operations of calculating an example topic count number coherence score in accordance with embodiments of the present disclosure.

The example method 800 may start at step/operation 802. In some examples, the step/operation 802 may be subsequent to the step/operation 703 of FIG. 7, where a computing entity may determine the plurality of topic variables.

At step/operation 804, a computing entity (such as the data object computing entity 105 described above in connection with FIG. 1 and FIG. 2) may include means (such as the processing element 205 of the data object computing entity 105 described above in connection with FIG. 2) for selecting a first topic variable group from the plurality of topic variables.

In some examples, the first topic variable group may be associated with a first topic count number. For example, the computing entity may select fourteen topic variables from the plurality of topic variables. In this example, the fourteen topic variables may form the first topic variable group, and the first topic count number may be fourteen. In some examples, the computing entity may select other number(s) of topic variables from the plurality of topic variables to form the first topic variable group.

At step/operation 806, a computing entity (such as the data object computing entity 105 described above in connection with FIG. 1 and FIG. 2) may include means (such as the processing element 205 of the data object computing entity 105 described above in connection with FIG. 2) for calculating a topic coherence score for each topic variable in the first topic variable group.

In the present disclosure, the term "topic coherence score" refers to a value that may represent a coherence level associated with a topic variable for a text field. In some examples, the topic coherence score may be calculated/determined/predicted based on one or more machine learning model(s), statistical model(s), and/or natural language processing model(s), including, but not limited to, the LDA model described above.

Continuing from the above example, when the first topic variable group comprises fourteen topic variables, the computing entity may calculate/determine/predict a topic coherence score for each of the fourteen topic variables. As an example, Table 1 below illustrates example topic coherence scores for a group of fourteen topic variables:

TABLE 1

Example Topic Variables and Topic Coherence Scores

| Topic Variable | Topic Coherence Score |
|---|---|
| Topic 1 | 0.02 |
| Topic 2 | 0.3 |
| Topic 3 | 0.8 |
| Topic 4 | 0.7 |
| Topic 5 | 0.7 |
| Topic 6 | 0.03 |
| Topic 7 | 0.4 |
| Topic 8 | 0.2 |
| Topic 9 | 0.5 |
| Topic 10 | 0.5 |
| Topic 11 | 0.06 |
| Topic 12 | 0.4 |
| Topic 13 | 0.06 |
| Topic 14 | 0.02 |

At step/operation 808, a computing entity (such as the data object computing entity 105 described above in connection with FIG. 1 and FIG. 2) may include means (such as the processing element 205 of the data object computing entity 105 described above in connection with FIG. 2) for calculating a first topic count number coherence score for the first topic count number.

In some examples, the computing entity may calculate/determine/predict the first topic count number coherence score based at least in part on the topic coherence score for each topic variable in the first topic variable group that is calculated/determined/predicted at step/operation 806. In some examples, the first topic count number coherence score may be calculated/determined/predicted as an average or mean value of topic coherence score(s) associated with topic variable(s) in the first topic variable group. Continuing from the above example illustrated in Table 1, the computing entity may calculate/determine/predict the first topic count number coherence score based on the following equation:

$$TCNCS_{14} = \sum_{i=1}^{14} TCS_i \div 14$$

$$= \frac{0.02 + 0.3 + 0.8 + 0.7 + 0.7 + 0.03 + 0.4 + 0.2 + 0.5 + 0.5 + 0.06 + 0.4 + 0.06 + 0.02}{14}$$

$$= 0.335$$

where $TCNCS_{14}$ represents first topic count number coherence score for fourteen topic variables, $TCS_i$ represents a topic coherence score for each topic variable. In this example, the first topic count number coherence score is 0.335.

In some examples, the first topic count number coherence score may be calculated/determined/predicted as a mode value of the topic coherence score(s) associated with topic variable(s) in the first topic variable group. In some examples, the first topic count number coherence score may be calculated/determined/predicted as a standard deviation value of the topic coherence score(s) associated with topic variable(s) in the first topic variable group. In some examples, other statistical values of the topic coherence score(s) may be used to calculate/determine/predict the first topic count number coherence score.

The method 800 may end at step/operation 810.

Referring back to FIG. 7, as described above, the computing entity may include means for calculating a plurality of topic count number coherence scores associated with the plurality of topic variables at step/operation 705 based on, for example but not limited to, method 800 described above in connection with FIG. 8.

In some examples, the computing entity may iterate through different values for the topic count number based on the plurality of data objects in accordance with, for example but not limited to, method 800 described above in connection with FIG. 8, and may calculate/determine/predict a topic count number coherence score for each topic count number. For example, if a total number of twenty-four topic variables are determined at step/operation 703, the computing entity may select one topic variable, calculate/determine/predict a topic count number coherence score for a topic count number of one, select two topic variables, calculate/determine/predict a topic count number coherence score for a topic count number of two, . . . , until all possible selections of topic variables and their corresponding topic count number coherence scores are calculated/determined/predicted. As such, a plurality of topic count number coherence scores associated with the plurality of topic variables may be calculated/determined/predicted.

At step/operation 707, a computing entity (such as the data object computing entity 105 described above in connection with FIG. 1 and FIG. 2) may include means (such as the processing element 205 of the data object computing entity 105 described above in connection with FIG. 2) for determining a highest topic count number coherence score from the plurality of topic count number coherence scores.

Continuing from the example above, if a total number of twenty-four topic variables are determined at step/operation 703, the computing entity may calculate/determine/predict a plurality of topic count number coherence scores associated with the twenty-four topic variables. As an example, Table 2 below illustrates some example topic count number coherence scores and their corresponding topic count numbers:

TABLE 2

Example Topic Count Number and Topic Count Number Coherence Score

| Topic Count Number | Topic Count Number Coherence Score |
| --- | --- |
| 12 | 0.5601 |
| 14 | 0.5914 |
| 16 | 0.5475 |
| 18 | 0.54 |
| 20 | 0.5334 |
| 22 | 0.5493 |
| 24 | 0.5441 |

As shown in TABLE 2, the highest topic count number coherence score may be 0.5914.

At step/operation 709, a computing entity (such as the data object computing entity 105 described above in connection with FIG. 1 and FIG. 2) may include means (such as the processing element 205 of the data object computing entity 105 described above in connection with FIG. 2) for selecting a corresponding topic count number associated with the highest topic count number coherence score as the optimal topic count number.

Continuing from the example illustrated in Table 2 above, the highest topic count number coherence score may be 0.5914, and the corresponding topic count number associated with the highest topic count number coherence score may be 14. In this example, the computing entity may determine that the optimal topic count number associated with the plurality of data objects may be fourteen.

The example method 700 may end at step/operation 711.

Referring back to FIG. 6, as described above, the computing entity may include means for calculating an optimal topic count number at step/operation 612 based on, for example but not limited to, method 700 described above in connection with FIG. 7.

In some examples, subsequent to calculating an optimal topic count number, a computing entity (such as the data object computing entity 105 described above in connection with FIG. 1 and FIG. 2) may determine the relevance of the topic variables associated with the optimal topic count number in a particular domain. For example, when the data objects are associated with a healthcare FWA investigation system as described above, the computing entity may implement machine learning models and/or artificial intelligence algorithms to determine relevance levels of these topic variables in the domain of healthcare FWA investigation. Example machine learning models and/or artificial intelligence algorithms may include (but not limited to) those described above.

In some examples, if the computing entity determines that a relevance level of topic variable satisfies a relevance threshold for the domain, the computing entity may maintain the topic variable in the plurality of topic variables associated with a plurality of data objects (for example, those determined in connection with step/operation 703 of FIG. 7 described above).

In some examples, if the computing entity determines that a relevance level of topic variable does not satisfy a relevance threshold for the domain, the computing entity may remove the topic variable from the plurality of topic variables associated with a plurality of data objects (for example, those determined in connection with step/operation 703 of FIG. 7 described above. Subsequently, the computing entity may iterate through the step/operations of FIG. 7 and/or the steps/operations of FIG. 6 to calculate/determine/predict a new optimal topic count number.

The example method 600 may end at step/operation 614.

As described above, a computing entity (such as the data object computing entity 105 described above in connection with FIG. 1 and FIG. 2) may include means (such as the processing element 205 of the data object computing entity 105 described above in connection with FIG. 2) for generating a base data table. The base data table may comprise one or more topic variables associated with the text field of each of the plurality of data objects. In some examples, the one or more topic variables may be associated with an optimal topic count number, which may be calculated/determined/predicted based on, for example but not limited to, method 600 shown in FIG. 6, method 700 shown in FIG. 7, and/or method 800 shown in FIG. 8.

Continuing from the example shown in Table 2 above, the computing entity may determine that the optimal topic count number is fourteen based on, for example, the topic count number coherence score associated with a group of fourteen topic variables (which may be calculated/determined/predicted based on the method 800 shown in FIG. 8) as being the highest topic count number coherence score (as described in connection with method 700 of FIG. 7). In such an example, the computing entity may include the fourteen topic variables in the base data table.

Additionally, or alternatively, a computing entity (such as the data object computing entity 105 described above in connection with FIG. 1 and FIG. 2) may include means (such as the processing element 205 of the data object computing entity 105 described above in connection with FIG. 2) for generating other metrics based at least in part on the plurality of data objects for a base data table. For example, the base data table may comprise at least one of: provider metric, lead metric, demographics, lead source, referral type, business area, allegation type, or taxonomy. As an example, Table 3 below illustrates example metrics in an example base data table generated based on data objects in a healthcare FWA investigation system for invaginating suspected FWA by a healthcare provider:

TABLE 3

Example Metrics of an Example Base Data Table

| Metric Type | Description |
| --- | --- |
| Topic Variables | Topic variables associated with an optimal topic count number |
| Provider Metrics | Number of data objects associated with a provider |
| Lead Metrics | Number of unique providers associated with a data object |
| Demographics Metrics | Location of the provider |
| Taxonomy Metrics | Provider taxonomy as captured in provider profile |

TABLE 3-continued

Example Metrics of an Example Base Data Table

| Metric Type | Description |
| --- | --- |
| Lead Source Metrics | The channel through which the lead(s), tip(s), and/or allegation(s) come from (e.g., from a member, from OIG, etc.) |
| Referral Type Metrics | The type of referral (e.g., data analytics) |
| Business Area Metrics | Line of business (e.g., M&R, C&S, E&I) |
| Allegation Type Metrics | Summary of the lead(s), tip(s), and/or allegation(s) that the data object represents |

While Table 3 above illustrates example metrics of an example base data table, it is noted that the scope of the present disclosure is not limited to those specific metrics only. In some examples, an example base data table in accordance with examples of the present disclosure may comprise less than or more than these metrics illustrated above.

In some examples, the computing entity may utilize the base data table to generate, train and/or select a predictive data model, examples details of which are provided below.

c. Exemplary Predictive Data Model Determination

Referring now to FIG. 9, an example method 900 illustrates example operations of determining a predictive data model in accordance with embodiments of the present disclosure. In particular, the method 900 illustrates an example "champion-challenger approach" to select a predictive data model from a plurality of predictive data models.

The method 900 may start at step/operation 901.

At step/operation 903, a computing entity (such as the data object computing entity 105 described above in connection with FIG. 1 and FIG. 2) may include means (such as the processing element 205 of the data object computing entity 105 described above in connection with FIG. 2) for generating a plurality of predictive data models based at least in part on the base data table.

In some examples, the plurality of predictive data models may include one or more machine learning models and/or artificial intelligence algorithms, such as, but not limited to, logistic regression model, gradient boosting machine, random forest, and/or naive Bayes, linear regression, decision tree, support vector machine (SVM), k-nearest neighbors algorithm (k-NN), K-means clustering, and/or the like.

In some examples, the computing entity may generate one or more training datasets for training the plurality of predictive data models. In some examples, these training datasets may be generated based on data and/or information obtained from the plurality of data objects in accordance with one or more data sampling techniques and/or one or more metrics in an example base data table.

For example, referring to Table 3 above, the computing entity may generate one or more datasets based on data sampled from the plurality of data objects in accordance with the topic variables metrics. For example, the computing entity may utilize coherence scores associated with topic variables (listed in the base data table) in the plurality of data objects as input for training the predictive data models.

Additionally, or alternatively, the computing entity may generate one or more datasets based on the plurality of data objects in accordance with the provider metrics. For example, a computing entity may calculate/determine/predict a number of data objects that each provider name/identifier is associated with (based on provider name/identifier fields of these data objects), and may provide these numbers as input for training the predictive data models.

Additionally, or alternatively, the computing entity may generate one or more datasets based on the plurality of data objects in accordance with the demographics metrics and/or the taxonomy metrics. For example, a computing entity may retrieve provider profiles based on provider name/identifier fields of these data objects, and may provide demographics and/or taxonomy information from provider profiles as input for training the predictive data models.

Additionally, or alternatively, the computing entity may generate one or more datasets based on the plurality of data objects in accordance with the lead source metrics, the referral type metrics, and/or the business area metrics. For example, a computing entity may provide information from the lead source fields of the data objects as input for training the predictive data models. Additionally, or alternatively, the computing entity may provide information from the refer type fields of the data objects as input for training the predictive data models. Additionally, or alternatively, the computing entity may provide information from the category fields of the data objects an input for training the predictive data models.

Additionally, or alternatively, the computing entity may generate one or more datasets based on the plurality of data objects in accordance with the allegation type metrics. For example, a computing entity may provide information from the text fields of the data objects as input for training the predictive data models.

While the examples above illustrate generating one or more datasets for training the predictive data models, it is noted that the scope of the present disclosure is not limited to these datasets only. For example, a computing entity may generate datasets based on the plurality of data objects in accordance with some (but not all) metrics in the base data table. For example, while the example base data table in Table 3 illustrates nine metrics, it is noted the computing entity may select, for example, a subset of these metrics (for example, seven of the nine metrics) and generate datasets based on data objects in accordance with these seven metrics for training the predictive data models.

In some examples, the computing entity may use different sampling techniques to obtain data and/or information from the plurality of data objects for generating the datasets. Example sampling techniques may include, but is not limited to, random sampling, systematic sampling, convenience sampling, cluster sampling, etc.

At step/operation 905, a computing entity (such as the data object computing entity 105 described above in connection with FIG. 1 and FIG. 2) may include means (such as the processing element 205 of the data object computing entity 105 described above in connection with FIG. 2) for calculating at least one performance metrics for each of the plurality of predictive data models.

In some examples, the at least one performance metrics may evaluate the performance of the plurality of predictive data models generated at step/operation 905. Example performance metrics may include, but not limited to, Area Under the Curve (AUC), confusion metrics, lift and gain charts, and/or the like.

For example, the computing entity may generate one or more testing datasets based on data and/or information obtained from the plurality of data objects in accordance with one or more data sampling techniques and/or one or more metrics in an example base data table, similar to those described above in connection with generating training datasets. In some examples, the one or more testing datasets may be provided as input to the predictive data models, and the computing entity may calculate/determine/predict the performance metrics of these predictive data models in generating outputs based on the one or more testing datasets.

At step/operation 907, a computing entity (such as the data object computing entity 105 described above in connection with FIG. 1 and FIG. 2) may include means (such as the processing element 205 of the data object computing entity 105 described above in connection with FIG. 2) for selecting the predictive data model from the plurality of predictive data models.

In some examples, the selection of the predictive data model may be based at least in part on the at least one performance metrics described above in connection with step/operation 905 above. For example, the selected predictive data model ("a champion model") may be associated with a best performance metrics as compared to the performance metrics of other predictive data models ("challenger models").

In some examples, the selected predictive data model may be a logistic regression model. In some examples, the selected predictive data model may be a gradient boosting machine model. In some examples, the selected predictive data model may be a random forest data model. In some examples, the selected predictive data model may be a naive Bayes model.

As described above, each of the predictive data models may be trained using datasets that may be generated based on one or more data sampling techniques on data from the plurality of data objects that is obtained in accordance with one or more metrics in an example base data table. In some examples, the selected predictive data model may be trained based on data that is obtained in accordance with the lead source metrics, the referral type metrics, the business are metrics, the allegation type metrics, the demographics metrics, the provider metrics, and the topic variables metrics.

The method 900 may end at step/operation 909.

While method 900 described above illustrates example operations of determining a predictive data model, it is noted that the scope of the present disclosure is not limited to these example operations only. In some examples, other approach(es) may be implemented for selecting and/or generating a predictive data model.

In some embodiments, a computing entity (such as the data object computing entity 105 described above in connection with FIG. 1 and FIG. 2) may include means (such as the processing element 205 of the data object computing entity 105 described above in connection with FIG. 2) for calculating a risk score for each of the plurality of data objects based at least in part on the predictive data model and a corresponding data object. In some examples, the computing entity may receive a data object as an input, and may generate a risk score as an output. For example, the data object may comprise a text field indicating lead(s), tip(s), and/or allegation(s) associated with a suspect healthcare FWA. The computing entity may generate a predictive data model as described above, and may provide the text field to the predictive data model as input. The predictive data model may generate a risk score based on the input, similar to those described above.

As described above, the risk score may indicate a likelihood of successful outcome associated with the lead, the tip, and/or the allegation. In some examples, the computing entity may adjust the queue order of the plurality of data objects in the data processing queue based on the risk score, similar to those described above in connection with FIG. 5.

In some examples, when the computing entity receives a new data object (for example, generated based on lead(s), tip(s), and/or allegation(s) of suspected healthcare FWA), the computing entity may calculate/determine/predict a risk score for the data object, and may determine a queue order for the data object based on the risk score. For example, the computing entity may place the new data object in the data processing queue subsequent to other data object(s) with a higher risk score, but prior to other data object(s) with a lower risk score.

In some examples, the computing entity may calculate/determine/predict risk scores associated with existing data objects in the data processing queue, and may adjust the queue orders of these data objects based on their corresponding risk scores. For example, the computing entity may move data objects with a higher risk score to a higher place in the data processing queue, such that the data object may be processed before other data object(s) with a lower risk score.

In some examples, a feedback loop may be incorporated to improve the calculation of risk scores. For example, the computing entity may record the outcomes of each lead(s), tip(s), and/or allegation(s) as described in the data objects of the data processing queue. As described above, it is expected that lead(s), tip(s), and/or allegation(s) with a high risk score will have more successful outcomes than lead(s), tip(s), and/or allegation(s) with a low risk score. If lead(s), tip(s), and/or allegation(s) associated with a high risk score does not lead to a successful outcome, the predictive data model may be retrained. Following retraining the predictive data model, the computing entity may measure the increase in performance using the feedback loop (for example, using the equation provided below).

In accordance with various examples of the present disclose, the implementations of predictive modeling and risk scores may lead to healthcare expense savings. For example, the following equation may be used to calculate/determine/predict a performance metrics of a system in accordance with the present disclosure:

$$p = \sum_{i=1}^{n} \text{exposure}_i * \frac{\text{risk}_i}{\alpha(t_{1i} - t_{0i}) + 1}$$

In the above equation, risk is the risk score calculated/determined/predicted by the predictive data model, a is the conceptual loss due to healthcare FWA per day, $t_{1i}$ may be the current time, $t_{0i}$ may be the time that the lead(s), tip(s), and/or allegation(s) was submitted to the healthcare FWA investigation system, and $\text{exposure}_i$ may be a particular provider exposure over the total number of members.

In some examples, based on the risk scores and the data processing queue, potential actions can be taken to minimize cost due healthcare FWA, which may include a recommendation that the provider be considered for immediate interventions. In the most urgent cases, a hard stop on claims payments may be implemented based on the risk score. Other options can include mandatory medical record requests for either some or all claims, or a referral for a full post-payment investigation of the provider's aberrant claims.

d. Exemplary User Interface

Referring now to FIG. 10, FIG. 11, and FIG. 12, example user interfaces are illustrated FIG. 10 illustrates an example user interface 1000 that may provide an example rendering of a data processing queue and/or data objects in accordance with examples of the present disclosure.

The example user interface 1000 may comprise a navigation section 1002, which may provide different options for rendering the data processing queue and/or the data objects. In the example shown in FIG. 10, the navigation section 1002 may provide options for rendering the data processing queue and/or the data objects in a "queue overview" interface, a "tip queue" interface or a "tip detail" interface. The "queue overview" interface may provide a summary of the data processing queue and the data objects, which may include a statistics overview of the data processing queue and the data objects. An example "queue overview" interface is illustrated and described in connection with FIG. 10.

The "tip queue" interface may provide a listing of one or more data objects in the data processing queue and may provide one or more options for filtering these data objects. An example "tip queue" interface is illustrated and described in connection with FIG. 11. The "tip detail" interface may provide details of one or more data objects in the data processing queue, which may include one or more fields associated with the one or more data objects. An example "tip detail" interface is illustrated and described in connection with FIG. 12

Referring back to FIG. 10, an example user interface 1000 may include one or more statistics sections that may indicate statistics of data objects associated with the data processing queue. As described above, each of the data objects may represent lead(s), tip(s), and/or allegation(s) associated with suspected healthcare FWA. In some examples, the example user interface 1000 may comprise a statistics section 1004, a statistics section 1006, a statistics section 1007, and a statistics section 1008.

In the example shown in FIG. 10, the statistics section 1004 may provide an overview of the statistics of data objects. For example, the statistics section 1004 may indicate the total number of data objects (i.e. "cases") that are in the data processing queue. The statistics section 1004 may indicate the average number of days that the data objects have been placed in the data processing queue. The statistics section 1004 may indicate the number of data objects labeled as high risk (for example, based on the risk scores calculated/determined/predicted by the predictive data model as described above).

In the example shown in FIG. 10, the statistics section 1006 may separate numbers of data objects based on their corresponding lines of business. For example, the statistics section 1006 may indicate the number of data objects that are associated with Medicare and retirement (M&R) (i.e. lead(s), tip(s), and/or allegation(s) that come from the M&R line of business). The statistics section 1006 may indicate the number of data objects that are associated with community and state (C&S) (i.e. lead(s), tip(s), and/or allegation(s) that come from the C&S line of business). The statistics section 1006 may indicate the number of data objects that are associated with employer and individual (E&I) (i.e. lead(s), tip(s), and/or allegation(s) that come from the E&I line of business).

In the example shown in FIG. 10, the statistics section 1007 may provide separate numbers of data objects based on their corresponding tip source. For example, the statistics section 1007 may indicate the number of data objects that are member driven (i.e. lead(s), tip(s), and/or allegation(s) that are submitted by a user as described above). The statistics section 1007 may indicate the number of data objects that are data driven (i.e. lead(s), tip(s), and/or allegation(s) that are generated based on data analytics of data patterns). The statistics section 1007 may indicate the number of data objects that are not member driven or data driven.

In the example shown in FIG. 10, the statistics section 1008 may provide separate numbers of data objects based on their received/created dates. For example, the statistics section 1008 may indicate the number of data objects that are created less than 30 days ago (e.g., lead(s), tip(s), and/or allegation(s) that are received less than 30 days ago). The statistics section 1008 may indicate the number of data objects that are created between 30 days ago and 45 days ago (e.g., lead(s), tip(s), and/or allegation(s) that are received between 30 days ago and 45 days ago). The statistics section 1008 may indicate the number of data objects that are created more than 45 days ago (e.g., lead(s), tip(s), and/or allegation(s) that are received more than 45 days ago).

In some examples, an example user interface 1000 may comprise one or more statistic filtering sections for filtering the data objects. In the example shown in FIG. 10, the example user interface 1000 may comprise a case status filter section 1010, which may comprise one or more radio buttons that allow a user to display statistics of data objects having the selected case status (e.g., "not started," "in progress") in the statistics sections, such as in the statistics section 1004, the statistics section 1006, the statistics section 1007, and/or the statistics section 1008. The example user interface 1000 may comprise a line of business filter section 1012, which may comprise one or more radio buttons that allow a user to display statistics of data objects having the selected line of business (e.g., "all lines of businesses," "M&R," "C&S," "E&I") in the statistics sections, such as in the statistics section 1004, the statistics section 1006, the statistics section 1007, and/or the statistics section 1008.

In some examples, the example user interface 1000 may comprise a data object distribution section 1014. In some examples, a computing entity (such as the data object computing entity 105 described above in connection with FIG. 1 and FIG. 2) may calculate/determine/predict a risk score for each of the plurality of data objects (for example, based on the example methods 500, 600, 700, 800, and/or 900 described above), and may generate a distribution chart illustrating the distribution of risk scores among these data objects in the data object distribution section 1014. In the example shown in FIG. 10, the distribution chart may be in the form of a bar chart. The x axis of the bar chart may indicate a risk score or a risk score range, and the y axis of the bar chart may indicate a number of data objects having the risk score and/or the risk score range. In some examples, each of the risk score or risk score range may be associated with a risk category (e.g., high, medium, low), and the distribution chart may illustrate data objects associated with each risk category (for example, via the legend associated with each bar in the bar chart as shown in FIG. 10).

FIG. 11 illustrates an example user interface 1100 that may provide an example rendering of a data processing queue and/or data objects in accordance with examples of the present disclosure.

The example user interface 1100 may comprise a navigation section 1101, similar to the navigation section 1002 described above in connection with FIG. 10. In particular, FIG. 11 may illustrate an example "tip queue" interface as described above.

In some examples, the example user interface 1100 may comprise a data object listing section 1105, which may provide a listing of data objects associated with the data processing queue. The listing may be in tabular format with each row representing a particular data object, and each column representing a particular field of the data object, such as the status, the data object identifier, the risk category, the provider identifier associated with the data object, the provider name associated with the data object, the number of data objects associated with each provider, the demographics of the provider, the number of days that the data object has been generated, the risk score associated with the data object, and the name of the investigator that is assigned to review the data object.

In some examples, the example user interface 1100 may comprise a listing navigation section 1109, which may allow a user to navigate one or more pages in the data object listing section 1105. In some examples, the example user interface 1100 may comprise a report generation button 1107. When a user clicks, taps, or otherwise selects the report generation button 1107, a computing entity (such as the data object computing entity 105 described above in connection with FIG. 1 and FIG. 2) may generate a report of data objects in the data object listing section 1105.

In some examples, the example user interface 1100 may comprise a data object filtering section 1103, which may provide one or more options for filtering the data objects in the data object listing section 1105. For example, the data object filtering section 1103 may provide options for filtering the data objects based on priority, line of business, specialty type, link status, referral source, and/or investigation status associated with these data objects.

FIG. 12 illustrates an example user interface 1200 that may provide an example rendering of a data processing queue and/or data objects in accordance with examples of the present disclosure.

The example user interface 1200 may comprise a navigation section 1202, similar to the navigation section 1002 described above in connection with FIG. 10. In particular, FIG. 12 may illustrate an example "tip detail" interface as described above.

In some examples, the example user interface 1200 may comprise a data object details section 1204, which may provide details associated with a data object in the data processing queue. For example, the details associated with the data object may be generated based on one or more fields associated with the data object, including, but not limited to, the status field, the identifier field, the risk category field, the provider name field, the provider identifier field, the risk score field, the investigator field, and/or the like. In some examples, the data object details section 1204 may comprise a description of the lead(s), tip(s), and/or allegation(s) based on, for example, the text field of the data object.

In some examples, the example user interface 1200 may comprise a data object timeline section 1206, which may indicate one or more milestone dates and/or time points associated with the data object (for example, the date/time when the lead(s), tip(s), and/or allegation(s) is received, the date/time when the lead(s), tip(s), and/or allegation(s) is entered into the data processing queue, and/or the date/time when the lead(s), tip(s), and/or allegation(s) is reviewed by the assigned investigator).

In some examples, the example user interface 1200 may comprise an associated member tips section 1208, which may provide information related to other data object(s) that may be associated with the data object presented in the data object details section 1204. In some examples, the example user interface 1200 may comprise a linked tip info section 1210, which may provide information related to other provider(s) that may be associated with the data object presented in the data object details section 1204.

V. CONCLUSION

Many modifications and other embodiments of the disclosure set forth herein will come to mind to one skilled in the art to which this disclosure pertain having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An apparatus comprising one or more processors and at least one non-transitory memory comprising a computer program code, the at least one non-transitory memory and the computer program code configured to, with the one or more processors, cause the apparatus to:
    retrieve a plurality of data objects associated with a data processing queue, wherein each data object of the plurality of data objects comprises a text field;
    generate a base data table based at least in part on the plurality of data objects, wherein the base data table comprises one or more topic variables associated with the text field of each of the plurality of data objects;
    select a predictive data model from a plurality of predictive data models, wherein (a) the plurality of predictive data models is generated based at least in part on the base data table, and (b) the predictive data model is selected from the plurality of predictive data models based at least in part on one or more performance metrics associated with the predictive data model;
    generate, using the predictive data model, a predictive risk score for each data object of the plurality of data objects;
    update each data object of the plurality of data objects to include a risk category field comprising a risk category based at least in part on a corresponding predictive risk score for the data object; and
    adjust a queue order of the plurality of data objects in the data processing queue based at least in part on the predictive risk score for each data object of the plurality of data objects.

2. The apparatus of claim 1, wherein the plurality of data objects is associated with a healthcare fraud, waste and abuse (FWA) investigation system, wherein the text field of each of the plurality of data objects comprises a healthcare fraud lead description.

3. The apparatus of claim 1, wherein, when generating the base data table based at least in part on the plurality of data objects, the at least one non-transitory memory and the computer program code are configured to, with the one or more processors, cause the apparatus to further:
    remove at least one of a punctuation element, a date element, or a Unicode element from the text field of each of the plurality of data objects.

4. The apparatus of claim 1, wherein, when generating the base data table based at least in part on the plurality of data objects, the at least one non-transitory memory and the computer program code are configured to, with the one or more processors, cause the apparatus to further:
    remove at least one stop-word from the text field of each of the plurality of data objects.

5. The apparatus of claim 1, wherein, when generating the base data table based at least in part on the plurality of data objects, the at least one non-transitory memory and the computer program code are configured to, with the one or more processors, cause the apparatus to further:
    determine an optimal topic count number based on the text field of each of the plurality of data objects, wherein the one or more topic variables are associated with the optimal topic count number.

6. The apparatus of claim 5, wherein, when determining the optimal topic count number, the at least one non-transitory memory and the computer program code are configured to, with the one or more processors, cause the apparatus to further:
   determine a plurality of topic variables based at least in part on a natural language processing model and the text field of each of the plurality of data objects; and
   determine a plurality of topic count number coherence scores associated with the plurality of topic variables, wherein each of the plurality of topic count number coherence scores is associated with a topic count number.

7. The apparatus of claim 6, wherein the natural language processing model is a Latent Dirichlet Allocation (LDA) model.

8. The apparatus of claim 6, wherein the at least one non-transitory memory and the computer program code are configured to, with the one or more processors, cause the apparatus to further:
   determine a highest topic count number coherence score from the plurality of topic count number coherence scores; and
   select a corresponding topic count number associated with the highest topic count number coherence score as the optimal topic count number.

9. The apparatus of claim 6, wherein, when determining the plurality of topic count number coherence scores associated with the plurality of topic variables, the at least one non-transitory memory and the computer program code are configured to, with the one or more processors, cause the apparatus to further:
   select a first topic variable group from the plurality of topic variables, wherein the first topic variable group is associated with a first topic count number;
   determine a topic coherence score for each topic variable in the first topic variable group; and
   determine a first topic count number coherence score for the first topic count number based at least in part on the topic coherence score for each topic variable in the first topic variable group.

10. The apparatus of claim 1, wherein the base data table comprises at least one of: provider metric, lead metric, demographics, lead source, referral type, business area, allegation type, or taxonomy.

11. The apparatus of claim 1, wherein, when determining the predictive data model based at least in part on the base data table, the at least one non-transitory memory and the computer program code are configured to, with the one or more processors, cause the apparatus to further:
   generate a plurality of predictive data models based at least in part on the base data table;
   determine at least one performance metrics for each of the plurality of predictive data models; and
   select the predictive data model from the plurality of predictive data models based at least in part on the at least one performance metrics.

12. The apparatus of claim 1, wherein the at least one non-transitory memory and the computer program code are configured to, with the one or more processors, cause the apparatus to further:
   determine a risk score for each of the plurality of data objects based at least in part on the predictive data model and a corresponding data object.

13. A computer-implemented method, comprising:
   retrieving, by one or more processors, a plurality of data objects associated with a data processing queue, wherein each data object of the plurality of data objects comprises a text field;
   generating, by the one or more processors, a base data table based at least in part on the plurality of data objects, wherein the base data table comprises one or more topic variables associated with the text field of each of the plurality of data objects;
   selecting, by the one or more processors, a predictive data model from a plurality of predictive data models, wherein (a) the plurality of predictive data models is generated based at least in part on the base data table, and (b) the predictive data model is selected from the plurality of predictive data models based at least in part on one or more performance metrics associated with the predictive data model;
   generating, by the one or more processors and using the predictive data model, a predictive risk score for each data object of the plurality of data objects:
   updating, by the one or more processors, each data object of the plurality of data objects to include a risk category field comprising a risk category based at least in part on a corresponding predictive risk score for the data object; and
   adjusting, by the one or more processors, a queue order of the plurality of data objects in the data processing queue based at least in part on the predictive risk score for each data object of the plurality of data objects.

14. The computer-implemented method of claim 13, wherein the plurality of data objects is associated with a healthcare fraud, waste and abuse (FWA) investigation system, wherein the text field of each of the plurality of data objects comprises a healthcare fraud lead description.

15. The computer-implemented method of claim 13, further comprising:
   removing at least one of a punctuation element, a date element, or a Unicode element from the text field of each of the plurality of data objects.

16. The computer-implemented method of claim 13, further comprising:
   removing at least one stop-word from the text field of each of the plurality of data objects.

17. The computer-implemented method of claim 13, further comprising:
   determining an optimal topic count number based on the text field of each of the plurality of data objects, wherein the one or more topic variables are associated with the optimal topic count number.

18. The computer-implemented method of claim 17, further comprising:
   determining a plurality of topic variables based at least in part on a natural language processing model and the text field of each of the plurality of data objects; and
   determining a plurality of topic count number coherence scores associated with the plurality of topic variables, wherein each of the plurality of topic count number coherence scores is associated with a topic count number.

19. The computer-implemented method of claim 18, wherein the natural language processing model is a Latent Dirichlet Allocation (LDA) model.

20. At least one non-transitory computer-readable storage medium having computer-readable program code portions stored therein, the computer-readable program code portions comprising an executable portion configured to:

retrieve a plurality of data objects associated with a data processing queue, wherein each data object of the plurality of data objects comprises a text field;

generate a base data table based at least in part on the plurality of data objects, wherein the base data table comprises one or more topic variables associated with the text field of each of the plurality of data objects;

select a predictive data model from a plurality of predictive data models, wherein (a) the plurality of predictive data models is generated based at least in part on the base data table, and (b) the predictive data model is selected from the plurality of predictive data models based at least in part on one or more performance metrics associated with the predictive data model;

generate, using the predictive data model, a predictive risk score for each data object of the plurality of data objects;

update each data object of the plurality of data objects to include a risk category field comprising a risk category based at least in part on a corresponding predictive risk score for the data object; and adjust a queue order of the plurality of data objects in the data processing queue based at least in part on the predictive risk score for each data object of the plurality of data objects.

* * * * *